No. 11,986. Reissued May 13, 1902

R. P. KUHN.

FORMALDEHYDE LAMP.

(Application filed Apr. 14, 1902.)

2 Sheets—Sheet 1.

WITNESSES:
Fenton S. Pelt,
Grace P. Brereton.

INVENTOR
Richard P. Kuhn
BY Sturtevant & Greeley
Attorneys

No. 11,986. Reissued May 13, 1902.

R. P. KUHN.

FORMALDEHYDE LAMP.

(Application filed Apr. 14, 1902.)

2 Sheets—Sheet 2.

WITNESSES:

Fenton S. Pelt,

Grace P. Brereton

INVENTOR

Richard P. Kuhn

BY Sturtevant & Greeley

Attorneys

UNITED STATES PATENT OFFICE.

RICHARD P. KUHN, OF ALEXANDRIA, VIRGINIA, ASSIGNOR TO THE KUHN FORMALDEHYDE GENERATING COMPANY, A CORPORATION OF VIRGINIA.

FORMALDEHYDE-LAMP.

SPECIFICATION forming part of Reissued Letters Patent No. 11,986, dated May 13, 1902.

Original No. 666,103, dated January 15, 1901. Application for reissue filed April 14, 1902. Serial No. 102,810.

*To all whom it may concern:*

Be it known that I, RICHARD P. KUHN, residing at Alexandria, in the county of Alexandria and State of Virginia, have invented certain new and useful Improvements in Formaldehyde-Lamps, of which the following is a specification.

This invention is in the nature of an improved means for generating formaldehyde gas, and the same more particularly refers to that type of generating-lamp disclosed in my Patent No. 599,849, dated March 1, 1898.

My present invention seeks to provide certain improvements having for their purpose to simplify the construction of my patented lamp, cheapen the cost of manufacture, and render it more effective in its use.

My invention comprehends in its complete make-up a novel arrangement of the upper diaphragm-holder or oxidizing-chamber and its peculiar combination with the base or burner portion, whereby the oxidizing or generating chamber can be quickly and conveniently raised vertically and swung laterally in a horizontal plane to allow for a ready access to the burner, and it also includes a simple means for adjustably supporting the oxidizing-chamber, having the platinized diaphragm over the burner during the operation of heating the diaphragm.

Again, this invention seeks to provide an improved arrangement of oxidizing or generating chamber whereby a greater percentage of formaldehyde gas is obtainable than is capable of being produced by the construction of parts disclosed in my patented lamp aforesaid, the said improved construction of oxidizing-chamber also including a pair of conical platinized diaphragms having for their purpose to provide an increased area of heat-absorbing surface without increasing the diameter of the body of the oxidizing-chamber.

In its more subordinate features my invention consists in certain details of construction and novel arrangement of parts, which will hereinafter be fully explained and particularly pointed out in the appended claims, reference being had to the accompanying drawings, in which—

Figure 1:
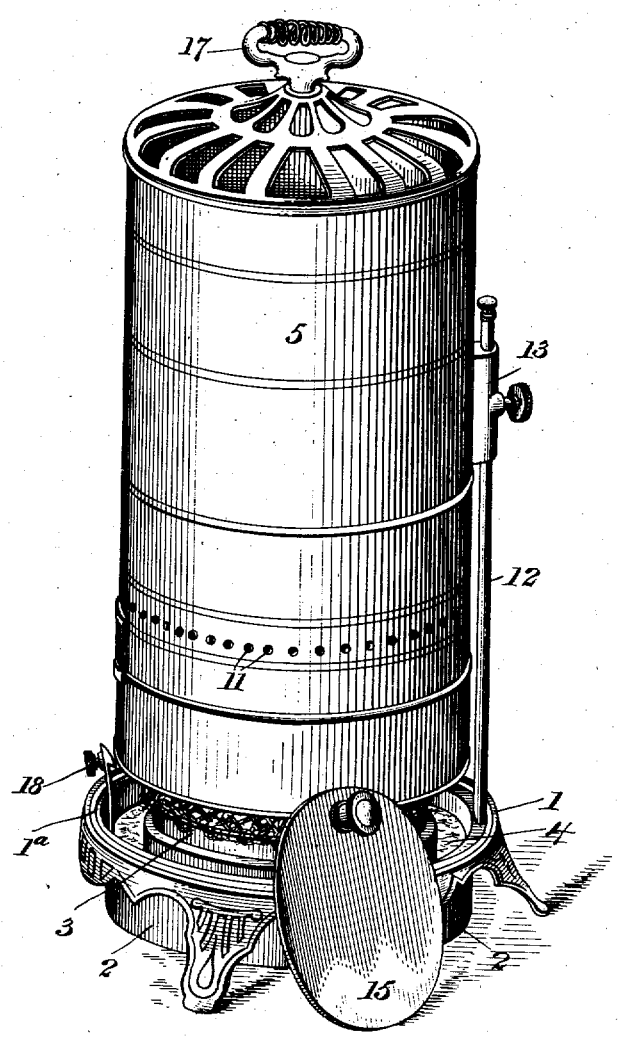
Figure 2:
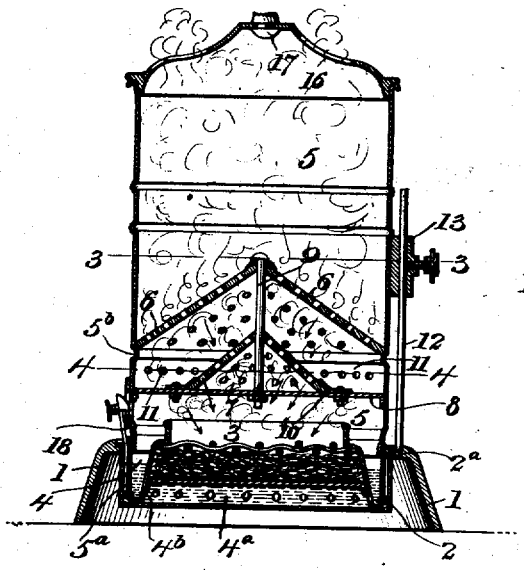
Figure 3:
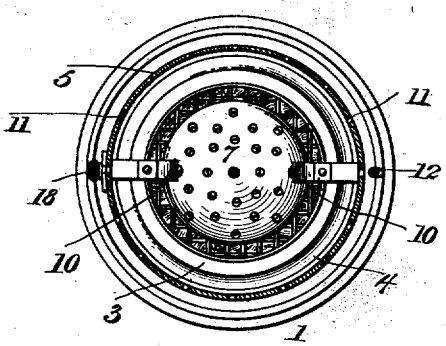
Figure 4:
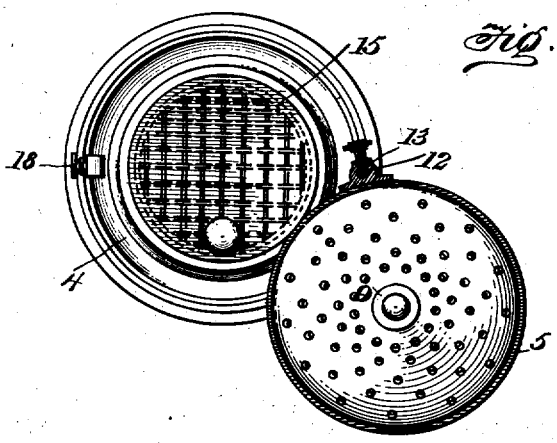

Figure 1 is a perspective view of my lamp, the oxidizing-chamber being shown in the position it is held during the heating of the platinized diaphragm. Fig. 2 is a vertical section of the lamp, the parts being in position to generate formaldehyde. Fig. 3 is a horizontal section taken on the line 3 3 of Fig. 2. Fig. 4 is a similar section on the line 4 4 of Fig. 2, the oxidizing-chamber being shown swung laterally, the muffler-plate being shown in its operating position for choking the burner-flame.

In its practical construction my present form of formaldehyde-lamp comprises generally a base, in which is held a burner-pan, an oxidizing-chamber detachably mounted over the burner-pan and held for vertical adjustment, means being also provided for holding the said oxidizing-chamber in its vertical adjusted positions and for permitting the said chamber being swung laterally in a horizontal plane, said oxidizing-chamber being pivotally supported over the burner-pan in such manner that the said chamber can be readily swung laterally when lifted up to a point above the burner-pan.

Referring now to the details of construction, 1 designates a suitably shaped and ornamented base provided with an annular internal rim $1^a$, which forms a supporting-ledge for the outturned rim $2^a$ of the water-pan 2. Within the pan 2 is held a burner-pan 3, said pan being of a diameter less than that of the water-pan 2, whereby a water-space 4 is provided, which surrounds the burner-pan, as clearly shown in Fig. 2, by reference to which it will also be observed the bottom of the burner-pan does not extend down to the bottom of the pan 2, such arrangement producing a water-space $4^a$ under the burner-pan, which communicates through a series of openings $4^b$ with the water-space 4, the reason for which will presently appear.

5 designates the body portion of my lamp, which is formed of sheet metal and is preferably cylindrical, its lower end being of a diameter to snugly extend down into the annular water-space surrounding the burner when the parts are in the position shown in Fig. 2.

It is my practice in constructing the lamp to make the lower part of the body 5 (indicated at $5^a$) of copper, so that that portion of the body 5 surrounding the burner will remain very hot for a considerable length of time, thereby not alone aiding by reason of radiant heat to assist in evaporating the wood-spirit, but also serve to warm the water surrounding the pan, which by reason of its circulation under the bottom of the burner also becomes thoroughly heated and in consequence serves to help evaporate the wood-alcohol contained in the burner.

In my present form of lamp I provide two pervious catalytic diaphragms, an upper one 6 and a lower one 7, both of which have a conical shape, with their apexes uppermost, as clearly shown in Fig. 2. The object in making the diaphragms conical is twofold—first, it provides an increased heat collecting and reflecting surface, and, secondly, such form of diaphragms serve as draft-cones. The upper diaphragm 6 has its base of a diameter equal that of the body 5, said base being supported upon an inturned swaged rim $5^b$, forming a part of the said body 5. The lower disk 7 prevents a too great concentration of the radiant or reflected heat-rays upon the burner, and the said diaphragm 7 is of a less diameter than the diaphragm 6 to permit a free circulation of the heat and draft between the diaphragm 6 and the burner. The diaphragm 7 has its upper face platinized, the upper face being so treated to maintain the radiant heat qualities thrown off by the diaphragm 6.

From practical experience I have found the double diaphragm arrangement above described and illustrated in large-sized lamps very desirable, as the radiant heat from the upper disk is often very intense, and by the concentration of the saturated filling in the burner-pan frequently produces combustion. This is avoided by reason of said rays being deflected by the lowermost diaphragm 7.

The diaphragm 7 is supported upon cross-braces 8, and said diaphragm 7, together with the diaphragm 6, is held steady in its position by the vertical rod 9, the lower diaphragm 7 being further braced by cleats 10, secured to the brace 8, as shown.

To supply the necessary oxygen, the body 5 has a series of perforations 11 at a point between the two diaphragms 6 and 7.

12 denotes a standard projected up from the base 1, which forms a supporting member for the body 5 when elevated, the said body 5 having a vertical apertured lug 13 at one side, adapted to engage with and slide upon the standard 12, said lug having a clamp-screw 13 whereby to clamp the body on the standard when raised to any of its vertical adjustments.

While I prefer on the score of economy and simplicity to use a vertically-projecting standard or rod upon which to support the body 5 when raised up to its vertical position, (and the said means are also desirable, as it provides for easily swinging the body 5 laterally away from the base to allow for easy access to the burner-pan, as illustrated in Fig. 4, to permit the use of the small muffler-plate 15 for extinguishing the flame of the burner,) I do not desire to confine myself to such means for supporting the body 5, as any other equivalent devices may be used for the same purpose.

The upper part of the body 5 is open, and for neatness in design an ornamental slotted casting-plate 16 is made fast thereto, to which is secured a handle 17 for conveniently lifting the lamp from place to place, it being also understood that when the parts are fitted in position for generating gas, as shown in Fig. 2, a suitable spring-catch 18, made fast to the base, will lock the said body 5 to the base.

From the foregoing description, taken in connection with the accompanying drawings, it is thought the operation and advantages of my improved lamp will be readily apparent.

In use, to generate the gaseous formaldehyde the operator ignites the wood-alcohol in the burner-pan and adjusts the body 5 to the position shown in Fig. 1, said body being held sufficiently high above the pan to allow for free air circulation to insure the proper combustion at the burner. This position of parts is maintained until the diaphragms have been heated to the degree desired, when the body 5 is turned laterally to the position shown in Fig. 4 to allow the operator quickly placing the muffler-plate 15 over the burner-pan and smothering the flame. This being done, the body is then swung back over the pan and dropped down to the position shown in Fig. 2. The radiant heat from the platinized disks 6 and 7, assisted by the heated water in pan 2, is then sufficient to produce an evaporation of the wood-spirit in the burner-pan, which, coming in contact with oxygen admitted through the openings 11 and passing over the platinized faces of the disks 6 and 7, produces formaldehyde gas, that passes out through the diaphragm 6 and on through the open top of body 5.

My present type of lamp differentiates from my patented lamp particularly in the means for supporting the body 5 in its different vertical and lateral positions, in the means for heating the water sufficient to assist in evaporating the wood-spirit in the burner-pan, and the distinctive arrangement of the diaphragm.

Having thus described my invention, what I claim, and desire to secure by Letters Patent, is—

1. The combination in a formaldehyde-lamp of a water-pan, a frusto-conical burner-pan of less diameter than the water-pan, so arranged therein as to leave an annular water-space between it and the water-pan, means for so supporting the burner-pan within the water-pan as to leave a water-space between its bottom and the bottom of the water-pan in communication with the annular water-space, a body portion carrying a catalytic diaphragm and having its lower portion of a diameter greater than that of the burner-pan and extending down into the annular water-space, whereby the water contained in the water-pan is heated both by direct contact and by radiation from the catalytic diaphragm; substantially as described.

2. The combination in a formaldehyde-lamp of a water-pan, a burner-pan of less diameter than the water-pan and so arranged therein as to leave an annular water-space between it and the water-pan, means for so supporting the burner-pan as to leave a water-space between its bottom and the bottom of the water-pan in communication with the annular water-space, a body portion carrying a catalytic diaphragm and having its lower portion extending down into the annular water-space, whereby the water contained in the water-pan is heated both by direct contact with the body portion and by radiation from the catalytic diaphragm; substantially as described.

3. In a formaldehyde-lamp of the character described, the combination with the oxidizing-chamber and the burner arranged substantially as shown; of a platinized conical diaphragm held within the oxidizing-chamber, a second platinized diaphragm disposed between the first diaphragm and the burner, said second diaphragm being of a less diameter than the first diaphragm, whereby to deflect the heat-rays from the said first diaphragm, all being arranged substantially as shown and for the purposes described.

4. In a lamp of the character described, the combination with the base having a burner-pan; of a casing having an oxidizing-chamber, a platinized diaphragm held in the said chamber, said casing extending up from the base and adapted to normally rest with its lower edge surrounding the burner-pan, means for supporting the said casing to permit its being moved in a vertical plane to bring its entire lower edge in a plane above the burner-pan, whereby to permit of the insertion of a muffle-plate over the burner-pan, connecting devices for joining the said casing detachably with the base, said connecting devices including a pivotal joint to permit the said casing being swung laterally in a horizontal plane when the lower edge of the said casing is elevated in a plane above the burner-pan; substantially as shown and for the purposes described.

5. The combination in a lamp of the character described, with the burner-pan, and the oxidizing-chamber arranged above the pan; of an upper perforated platinized diaphragm extending entirely across the oxidizing-chamber and a lower platinized diaphragm of less diameter than the upper diaphragm, and means for supporting the lower diaphragm over the burner-pan, as specified.

6. The combination with the base, the burner-pan 3, the oxidizing-chamber, said chamber being open at the top and having a series of air-inlets at a point above the burner, of a platinized perforated diaphragm 6, held within the oxidizing-chamber at a point above the air-inlets and the perforated platinized diaphragm 7, held over the burner and at a point between the aforesaid air-inlets and the burner, as specified.

In testimony whereof I affix my signature in the presence of two witnesses.

RICHARD P. KUHN.

Witnesses:
H. C. PRICE,
DOUGLASS STUART.